United States Patent
Curtis

(10) Patent No.: US 10,078,035 B2
(45) Date of Patent: Sep. 18, 2018

(54) POST-PROBE UPSTREAM METERING PUMP FOR INSURING NGL PHASE CHANGE COMPLETION IN SAMPLE CONDITIONING

(71) Applicant: Mustang Sampling LLC, Ravenswood, WV (US)

(72) Inventor: Micah A. Curtis, Ravenswood, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 191 days.

(21) Appl. No.: 15/252,628

(22) Filed: Aug. 31, 2016

(65) Prior Publication Data

US 2017/0082524 A1 Mar. 23, 2017

Related U.S. Application Data

(60) Provisional application No. 62/220,550, filed on Sep. 18, 2015.

(51) Int. Cl.
*G01N 1/20* (2006.01)
*G01N 1/14* (2006.01)

(52) U.S. Cl.
CPC ....... *G01N 1/14* (2013.01); *G01N 2001/1445* (2013.01)

(58) Field of Classification Search
CPC .......... G01N 1/14; G01N 1/2035; G01N 1/44; G01N 2001/105; G01N 33/004
See application file for complete search history.

(56) References Cited

U.S. PATENT DOCUMENTS

| | | | |
|---|---|---|---|
| 3,053,077 A | 11/1962 | Tracht | |
| 3,421,336 A | 1/1969 | Lichtenberger | |
| 3,681,997 A * | 8/1972 | Allen | G01N 1/2035 73/863.61 |
| 4,436,245 A | 3/1984 | Nonnenmann et al. | |

(Continued)

FOREIGN PATENT DOCUMENTS

| | | |
|---|---|---|
| WO | 2012/145606 A2 | 10/2012 |
| WO | 2015123302 A1 | 8/2015 |

OTHER PUBLICATIONS

International Application No. PCT/US2016/050190, Notification of Transmittal of the International Search Report and the Written Opinion of the International Searching Authority, or the Declaration, dated Nov. 18, 2016.

(Continued)

*Primary Examiner* — Francis C Gray
(74) *Attorney, Agent, or Firm* — Cahn & Samuels, LLP

(57) ABSTRACT

A post-probe upstream metering pump for insuring phase change completion of a multi-phase fluid such as Natural Gas Liquid (NGL) in a sample conditioning system having a pipeline sample take-off probe for fluid extraction, a sample conditioning unit for conditioning the extracted fluid to a select range of temperature and pressure for analysis of the fluid sample by an associated analyzer without dew point dropout or phase separation, and a metering pump disposed in-line between the sample take-off probe and the sample conditioning unit to pressurize the fluid sample to condense into a substantially fully liquid phase and to reduce lag time between extraction and fluid sample conditioning.

20 Claims, 1 Drawing Sheet

(56) References Cited

U.S. PATENT DOCUMENTS

| | | | |
|---|---|---|---|
| 5,502,266 | A | 3/1996 | Hodson |
| 6,044,825 | A | 4/2000 | Carter |
| 7,162,933 | B2 | 1/2007 | Thompson et al. |
| 7,484,404 | B2 | 2/2009 | Thompson et al. |
| 8,056,399 | B2 | 11/2011 | Thompson et al. |
| 8,307,843 | B2 | 11/2012 | Patterson |
| 8,966,969 | B2 | 3/2015 | Kriel et al. |
| 9,285,299 | B2 | 3/2016 | Thompson |
| 2009/0151427 | A1 | 6/2009 | Thompson et al. |
| 2012/0011919 | A1 | 1/2012 | Kriel et al. |
| 2012/0048881 | A1 | 3/2012 | Drube |
| 2014/0000426 | A1 | 1/2014 | Rolston et al. |
| 2014/0018598 | A1 | 1/2014 | Pfeiffer et al. |
| 2014/0311213 | A1* | 10/2014 | Thompson ............... G01N 1/18 73/23.2 |
| 2015/0000426 | A1* | 1/2015 | Rolston .............. G01N 33/0016 73/863.11 |

OTHER PUBLICATIONS

"White Paper on Liquid Hydrocarbon Drop Out in Natural Gas Infrastructure," NGC+ Liquid Hydrocarbon Dropout Task Group, Feb. 28, 2005.

Technical White Paper "Sample Liquid Petroleum Gas (and other high vapor pressure gas/liquids)",Sentry Equipment Corp, Tec 1.621 Rev. 0.

International Search Report from PCT for International Application No. PCT/US2016/050190 dated Nov. 18, 2016.

\* cited by examiner

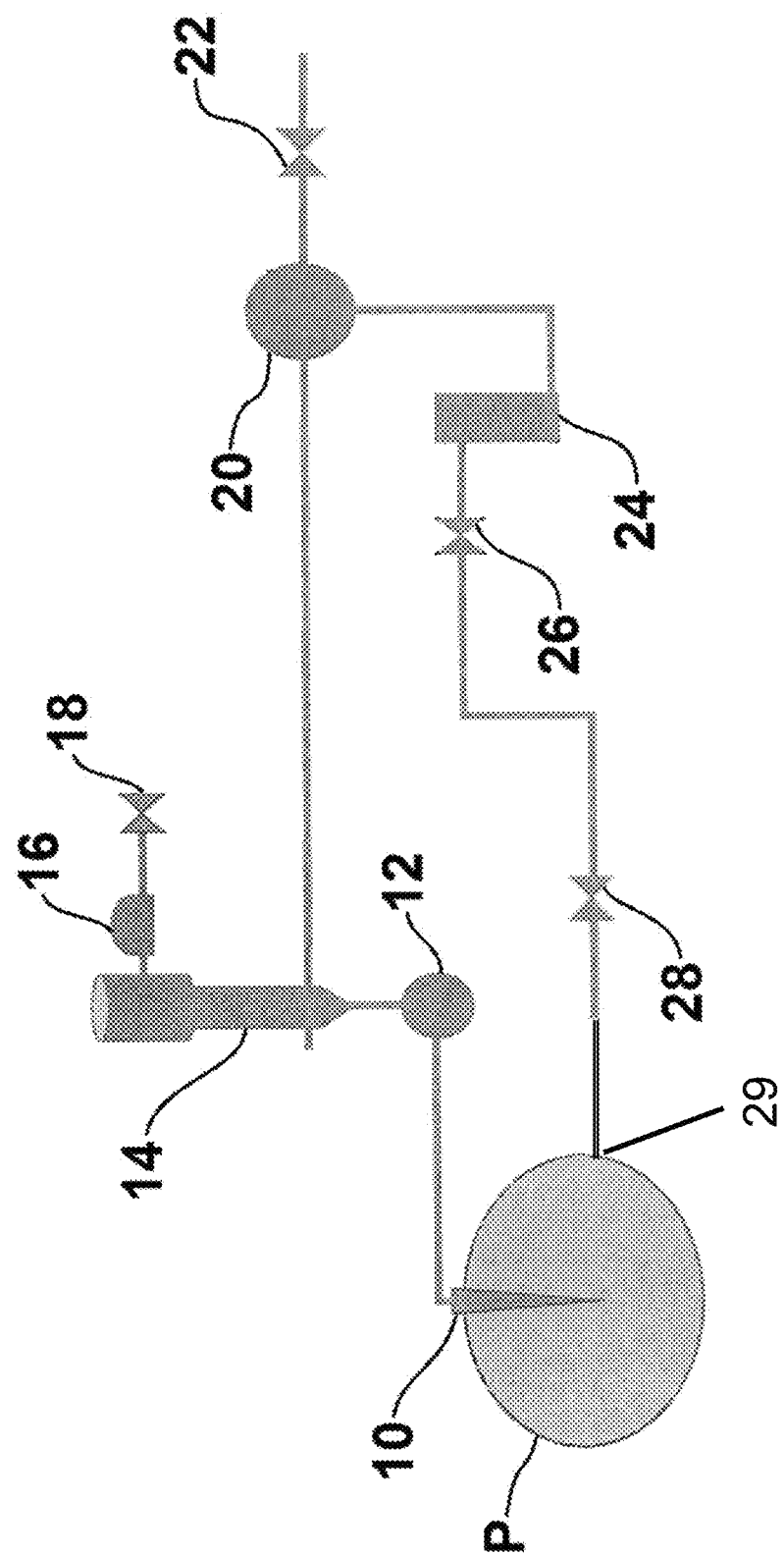

POST-PROBE UPSTREAM METERING PUMP FOR INSURING NGL PHASE CHANGE COMPLETION IN SAMPLE CONDITIONING

FIELD OF INVENTION

This invention relates to a system and method for enhancing accuracy and repeatability of measurements of a multi-phase fluid such as Natural Gas Liquids (NGL) component products extracted from a pipeline by a sample probe during sample analysis processing utilizing a metering pump upstream of sample conditioning equipment. The invention also reduces lag time of the pressurized fluid prior to introduction to the sample conditioning equipment. A further aspect of the invention is to generate sufficient residual pressure to off-set and overcome the takeoff vacuum (suction pressure) to promote unfiltered bypass flow for fluid reinjection into the pipeline.

BACKGROUND OF THE INVENTION

It is generally recognized in the gas processing industry that chromatographic and/or spectrographic analysis of a two or dual phase NGL fluid product cannot be performed accurately. During conventional fractionation or cryogenic separation processing, the conventional equipment either retains or generates entrained gas in the liquid product. Such is the case, in the first stage of NGL processing where such gas-entrained liquid is typically generated in an output from a cryogenic or de-methanizer tower and, particularly, during the "Ethane Recovery" phase. The resulting analysis of the sample fluid constituents/analytes, accordingly suffer from inaccuracies.

By way of explanation but not intending to be bound to any particular theory, it is believed that the cryogenic process leaves ethane in "dense" phase where the phase change to full liquid state is complete. Because of the substantial magnitude of volume difference of an NGL fluid between its liquid (droplet) form and its vaporized state, accurate and reproducible analysis by, for example, gas chromatography, is rendered almost impossible.

As such, there is a recognized need by processors of NGL for a system to achieve accurate and repeatable measurements usable for process control for NGL product quality assurance and for energy audits, particularly, in the case of custody transfer operations involving storage or transmission vessels.

SUMMARY OF THE INVENTION

It is an object of the present invention to overcome the shortcomings of the existing art.

It is another object of the present invention in certain embodiments to provide a solution to analysis of dual or multiphase NGL fluid.

Another object of the present invention in certain embodiments is to provide multi-phase liquid change completion.

Still another object of the invention in certain embodiments is to provide a system with enhanced accuracy and repeatable measurements for multi-phase fluids, such as NGL component products.

A further object of the invention in certain embodiments is to reduce sample lag time between takeoff and sample analysis.

Yet another object of the invention in certain embodiments is to produce sufficient residual pressure to off-set and overcome suction pressure within the pipeline for fluid reinjection of unfiltered bypass flow.

These and other objects are satisfied by a system for multi-phase fluid sample extraction, comprising: a) a sample take-off probe for extracting multi-phase fluid from a pipeline; b) a sample conditioning unit for vaporizing the extracted fluid sample and maintaining the vaporized sample in select temperature and pressure ranges to prevent dew point dropout and passing the conditioned vaporized sample to a downstream analyzer; and c) a metering pump disposed in-line between the sample take-off probe and the sample conditioning unit to increase pressure on and condense the extracted fluid sample to maximize transition of the multi-phase fluid sample into a single fully liquid phase.

The foregoing and still other objects are satisfied by a method for maximizing single state liquid sample of natural gas liquid extracted by means of a pipeline sample takeoff probe prior to vaporization for analysis using the metering pump, comprising the steps of: a) extracting a natural gas liquid fluid sample from a pipeline process stream through a sample take-off probe; b) pressurizing the extracted sample fluid to maximize complete condensation into a liquid phase; and c) communicating the pressurized liquid sample to a sample conditioner for vaporizing the liquid sample for passage from the sample conditioner to a downstream analyzer at a select pressure and temperature to minimize phase change.

In short, the invention contemplates a post-probe upstream metering pump for insuring multi-phase liquid phase change completion in a sample conditioning system, using a metering pump to pressurize the multi-phase fluid and maximize a single fully liquid state, as defined by a phase curve analysis.

The invention still further contemplates a combination of elements that comprise a post-probe upstream metering pump for insuring multi-phase liquid phase change completion in a sample conditioning system and a speed loop return line for reinjecting unused, pressurized multi-phase sample liquid into the original pipeline process stream.

The system of the present invention essentially comprises placement of a metering pump preferably with a coalescing filter disposed between a sample take-off source of a multi-phase liquid source, such as a pipeline, and a conditioning array for vaporizing the pressurized liquid sample for a downstream analyzer. The invention may also incorporate a filter bypass that elutes filtered sample to the downstream analyzer with a speed loop return for any excess unfiltered sample to the sample take-off source. The invention provides for feeding a fully liquid sample under pressure to the sample conditioner and thereby minimizes measurement anomalies generated by the presence of a liquid source containing multiple phase components.

In the NGL processing field, the present invention facilitates generation of a single phase fluid NGL product for nearly real-time analysis utilizing the metering pump located upstream of sample conditioning equipment. Practice of the invention provides pumping the fluid take-off sample to a select higher pressure prior to downstream sample conditioning and provides for inclusion of additional in-line filtering elements to maximize a complete transition from an NGL "dense" phase product to a substantially fully liquid product prior to conditioning. Such a transition not only optimizes the process through fast and accurate data, it also optimizes subsequent stages of processing by reducing carry-over of unwanted components from any previous stage of processing.

In addition to providing a substantially uniform liquid sample to the sample conditioner, the liquid which is subject to augmented pressure moves more rapidly through the system to thereby reduce the sample lag time between take-off and sample analysis, thereby improving both measurement speed and accuracy. Consequently, the invention enhances NGL process performance as a result of faster availability of useful data used to control the process and avoids system inaccuracies that can direct inappropriate product into storage or transmission vessels. Likewise, the invention permits sample take-off as close to the process as possible, a feature struggled with in the prior art due to the need for longer sample passages to assure near-as-completely-possible phase change to full liquid state.

The present invention also contemplates and solves the problem arising from pressure variability based on the particular composition of the subject fluid. Persons having ordinary skill in the art recognize that for any given source, the particular make-up of the sampled fluid varies. Adjusting the requirements for a particular fluid based on the source's composition and phase characteristics, which is readily determinable by convention through individual phase analysis, increases fluid homogeneity, minimizes sample phase separation, limits system lag time even in the case of an already single phase liquid, and maximizes the accuracy of the analysis.

Referring to the reduced lag time for sample transit provided by the invention, the velocity of the fluid increases which in turn reduces the opportunity for the single phase fluid to revert to a dual or multi-phase condition. Preferably, the process pressure is raised via the pump to a select value that is high enough to avoid the occurrence of "speed loop" or "liquid return to process".

The utilization of increased single phase liquid sample pressure also provides advantages such as increased operations flexibility by, for example, providing a capability for self-cleaning filtration and providing protection to downstream analyzers by minimizing the introduction of multiphasic fluids. A further benefit provided by the invention is that it avoids waste by allowing for reinjection of unneeded sample into the pipeline or process stream.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, "analyte" contemplates a constituent from a source such as multi-phase fluid, such as natural gas liquid, capable of vaporization and sample content characterization by conventional analysis equipment such as a gas chromatograph, mass spectrograph, Raman spectrophotometer, tunable diode laser spectrograph, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical, whether direct or indirect, affixed or adjustably mounted, as for example, the communication unit is connected to the a sample analyzer component either directly or through a conventional wireless linkage when spaced apart. Thus, unless specified, "connected" is intended to embrace any operationally functional connection.

As used herein, the term "multi-phase fluid" includes a stream comprising natural gas, hydrocarbon liquids in the form of a stream, and/or small discrete drops or droplets, vaporized hydrocarbon liquids, water in the form of a stream and/or droplets and water vapor.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein, the term "single phase liquid" connotes a stable liquid possessing a substantially uniform single phase that does not change state, e.g. vaporize.

As used herein, the term "speed loop" refers to a fluid transmission path originating at sample take-off and terminating at a point of fluid return to the process stream.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used herein "suction pressure" means the pressure of the fluid in the associated pipeline which may be as low as atmospheric.

In the following description, reference is made to the accompanying drawing, which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

BRIEF DESCRIPTION OF THE DRAWING

FIG. 1 is a schematic view of an embodiment of the invention.

DETAILED DESCRIPTION OF THE DRAWING

FIG. 1 illustrates a system for extracting an NGL sample from pipeline P via a probe 10, such as a Certiprobe® available from Mustang Sampling of Ravenswood, W. Va.

The fluid sample passes from the sample probe takeoff to and through a coalescing filter 12. A Collins Swirlklean Filter available from Collins Products Company of Livingston, Tex. is a commercially available product that provides a high pressure rated coalescing filter 12 meeting the operation requirements of the invention herein. The filter 12 is used to remove particulates to protect the metering pump 14 just downstream.

The metering pump 14 is preferably pneumatic and is associated with a conventional controller 16, which may be a pneumatic controller, incorporating feedback sensors and an air isolation valve 18. The controller 16 is preferably integrated with the metering pump 14 as one unitary assembly. A commercially available pneumatic metering pump 14 meeting this criteria is the V Dual Seal Plunger series available from the Williams, Milton Roy of Ivyland, Pa. The operating cycle of an example metering pump 14 is such that a power stroke displaces a precise amount of fluid corresponding to the stroke of a plunger, followed by a drop in pressure from a suction stroke which, again refills a fluid chamber for a subsequent power stroke. The flow of the metering pump 14 is, for example, adjusted by a pump setting gage. Likewise, multiplexing two or more metering pumps 14, having their inlets and outlets connected in parallel, further increases the process fluid flow rate. It is good design practice to install a check valve in the pump discharge line at the point where the sample enters the process line to prevent process fluid from reaching the metering pump 14.

The metering pump 14 may also be a manually operated pump capable of pressurizing the extracted sample to sufficiently generate and sustain a single phase liquid.

The discharge pressure of the metering pump 14 is selected to achieve at least two objectives. First, the pressure must be sufficient to deliver and maintain the liquid in a single state (as defined by a phase curve analysis) with a minimum of lag time to a filtered bypass 20. The bypass filter 20 directs the pressurized and filtered fully liquid sample through a regulator valve 22 for delivery thereof to the downstream analyzing equipment in a regulated manner, preferably following sample conditioning by for example, a Mustang Intelligent Vaporizing Sample Conditioning System (MIV-2) available from Mustang Sampling of Ravenswood, W. Va.

Secondly, the residual pressure threshold must be high enough to overcome the original flooded suction pressure, to thereby allow the unfiltered bypass flow through bypass filter 20 to be reinjected into the same pipeline P that the sample was extracted from. That unused, unfiltered liquid stream is directed through a flow meter 24, to measure a flow rate of the unused sample liquid, and further through a back pressure regulator 26, to regulate upstream reinjection pressure into the pipeline via pipeline reinjection port 29. The unused sample is then directed through an associated flow control metering valve 28 and is reinjected into the pipeline P by utilizing its higher pressure to overcome the pipeline pressure.

While not intended to be limiting as to relative parameters, in one embodiment of the invention the NGL in the pipeline P is at a temperature of 80° F. (~26° C.) and a suction pressure of 250 PSIG (~17 bar). The NGL sample mixture, at that temperature, must be at a pressure of 400 PSIG (~27.5 bar) in order to establish equilibrium in a stable liquid state. The discharge pressure is raised by the pump to 600 PSIG (~41 bar). The filtered sample passing out of the by-pass filter 20 is regulated to the required 400 PSIG for supply to the downstream analyzer(s). The unused, unfiltered product is reinjected into the pipeline P by utilizing its now higher pressure to overcome the pressure of the pipeline P.

Although the described embodiment of the invention and the variations thereof have been illustrated in the forgoing specification, it is understood by those skilled in the art that many modifications and embodiments of the invention will come to mind to which the invention pertains, having benefit of the teaching presented in the foregoing description and associated drawing. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

We claim:

1. A system for multi-phase fluid sample extraction, comprising:
   a) a sample take-off probe for extracting multi-phase fluid from a pipeline;
   b) a sample conditioning unit for vaporizing the extracted fluid sample and maintaining the vaporized sample in select temperature and pressure ranges to prevent dew point dropout and passing the conditioned vaporized sample to a downstream analyzer; and
   c) a metering pump disposed in-line between the sample take-off probe and the sample conditioning unit to increase pressure on and condense the extracted fluid sample to maximize transition of the multi-phase fluid sample into a single fully liquid phase.

2. The system of claim 1 further comprising a particulate coalescing filter disposed in-line between the sample take-off probe and the metering pump.

3. The system of claim 2 where the metering pump is a pneumatic pump.

4. The system of claim 3 where the pneumatic pump includes a pneumatic controller and an air isolation valve.

5. The system of claim 4 where the pneumatic controller includes at least one feedback sensor.

6. The system of claim 1 where the multi-phase fluid is natural gas liquid and further including a return loop to the pipeline.

7. The system of claim 6 where the metering pump generates a pressure of at least 400 PSIG.

8. The system of claim 6 where the metering pump generates pressure of at least 600 PSIG for reinjection of the pressurized, liquid natural gas liquid through the return loop into the pipeline to overcome suction pressure therefrom.

9. The system of claim 1 where the metering pump minimizes lag time from sample extraction to sample conditioning.

10. The system of claim 1 further comprising a filter member disposed in-line between the metering pump and the sample conditioning unit where said filter member includes a return loop to the pipeline.

11. The system of claim 10 further comprising a fluid flow regulator valve disposed in line between the filtered member and the sample conditioning unit.

12. The system of claim 10 further comprising a pipeline reinjection port and where the metering pump generates pressure of at least 600 PSIG to provide for reinjection of pressurized, liquid natural gas liquid through the return loop into the pipeline through said reinjection port.

13. The system of claim 12 further comprising a flow meter disposed in-line between said filter member and a reinjection port to measure a flow rate of liquid natural gas liquid passing therethrough.

14. The system of claim 13 further comprising a back pressure regulator disposed in-line between said filter member and said reinjection port to prevent liquid backflow into said filter member.

15. The system of claim 1 further including a return loop to the pipeline and where the multi-phase fluid is natural gas liquid and the metering pump generates pressure of at least 600 PSIG for reinjection of the pressurized, liquid natural gas liquid through the return loop into the pipeline to overcome suction pressure therefrom.

16. A method for maximizing single state liquid sample of natural gas liquid extracted by means of a pipeline sample take-off probe prior to vaporization for analysis using the metering pump, comprising the steps of:
 a) extracting a natural gas liquid fluid sample from a pipeline process stream through a sample take-off probe;
 b) pressurizing the extracted sample fluid to maximize complete condensation into a liquid phase; and
 c) communicating the pressurized liquid sample to a sample conditioner for vaporizing the liquid sample for passage from the sample conditioner to a downstream analyzer at a select pressure and temperature to minimize phase change.

17. The method of claim 16 where the system includes a coalescent filter element disposed between the sample take-off probe and the metering pump, and further comprising the step of passing the sample through the coalescent filter element to minimize passage of vapor and entrained gases contained in the multi-phase natural gas liquid to the metering pump.

18. The method of claim 17 where the system includes a filter member, a return loop, and a pipeline reinjection port where the metering pump pressurizes the extracted sample to at least 600 PSIG to provide for reinjection of pressurized, liquid natural gas liquid sample from the return loop through the pipeline reinjection port.

19. The method of claim 18 where the return loop includes an in-line back pressure regulating valve, the method further comprising the step of minimizing phase change from the liquid state of pressurized, liquid natural gas liquid sample passing through the filter member and to the reinjection port.

20. The method of claim 19 further comprising the step of minimizing lag time between sample extraction and extracted sample vaporization.

\* \* \* \* \*